US006522904B1

(12) United States Patent
Mika et al.

(10) Patent No.: US 6,522,904 B1
(45) Date of Patent: Feb. 18, 2003

(54) BIPOLAR SENSOR FOR MUSCLE TISSUE ACTION POTENTIAL DURATION ESTIMATION

(75) Inventors: Yuval Mika, Zichron Yaakov (IL); David Prutchi, Lake Jackson, TX (US)

(73) Assignee: Impulse Dynamics N.V., Curacao (NL)

( * ) Notice: Subject to any disclaimer, the term of this patent is extended or adjusted under 35 U.S.C. 154(b) by 0 days.

(21) Appl. No.: 09/280,486

(22) Filed: Mar. 30, 1999

(51) Int. Cl.$^7$ ................................................. A61B 5/04
(52) U.S. Cl. ........................ 600/374; 600/393; 600/509; 600/546
(58) Field of Search ................................. 600/374, 395, 600/393, 509, 546, 372; 607/5, 9, 4, 2, 115, 116, 119, 122, 123

(56) References Cited

U.S. PATENT DOCUMENTS

| | | | | |
|---|---|---|---|---|
| 4,365,639 A | * | 12/1982 | Goldreyer | 128/786 |
| 4,892,102 A | * | 1/1990 | Astrinsky | 128/642 |
| 4,955,382 A | * | 9/1990 | Franz et al. | 128/642 |
| 5,172,694 A | * | 12/1992 | Flammang et al. | 128/642 |
| 5,385,146 A | * | 1/1995 | Goldreyer | 128/642 |
| 5,405,375 A | * | 4/1995 | Ayers et al. | 607/122 |
| 5,534,022 A | * | 7/1996 | Hoffmann et al. | 607/122 |
| 5,755,761 A | * | 5/1998 | Obino | 607/122 |
| 5,931,863 A | * | 8/1999 | Griffin, III et al. | 607/122 |
| 6,152,882 A | * | 11/2000 | Prutchi | 600/509 |

FOREIGN PATENT DOCUMENTS

WO    WO 97/25098    7/1997

OTHER PUBLICATIONS

Seed et al., Relation of Human Cardiac Action Potential Duration to the Interval Between Beats: implications for the validity of rate corrected QT interval (QTc); British Heart Journal, 1987; 57:32–7.

Van Leeuwen, et al., Spatial Distribution of QT Intervals: An Alternative Approach to QT Dispersion,?.

Franz, et al., "Monophasic Action Potential Mapping in Human Subjects with Normal electrocardiograms: direct evidence for the genesis to the T wave", Circulation, vol. 75, No. 2, pp. 379–386, Feb. 1987.

* cited by examiner

Primary Examiner—Kennedy Schaetzle
(74) Attorney, Agent, or Firm—Reed Smith LLP

(57) ABSTRACT

A bipolar sensor for muscle tissue action potential duration estimation, in accordance with a preferred embodiment of the present invention, comprising two electrodes exposed at the distal end of an electrode lead. The electrodes at said distal end are kept at a very close proximity, and the sensor is electrically connected to a processing means for processing the signal detected by the sensor.

Another prefered embodiment of the bipolar sensor for muscle tissue action potential duration estimation comprises two electrodes positioned at a side wall of an electrode lead, wherein said electrodes are kept at a very close proximity, and wherein said sensor is electrically connected to a processing means for processing the signal detected by the sensor.

3 Claims, 5 Drawing Sheets

BIPOLAR SENSOR FOR MUSCLE TISSUE ACTION POTENTIAL DURATION ESTIMATION

FIELD OF THE INVENTION

The present invention relates to the estimation of action potential, and in particular action potential duration, of muscle tissues. More particularly it relates to a novel sensor designed for the chronic estimation of the local action potential duration, using close bipolar technique, in particular for cardiac purposes.

BACKGROUND OF THE INVENTION

The cardiac muscle is made of excitable tissue that can generate action potentials spontaneously or as a result of a stimulus. The electric potential invokes a mechanical response in the form of a contraction of the muscle tissue.

A single muscle twitch is characterized by a short period during which tension is being developed—the contraction phase. This is followed by a relaxation phase during which the muscle returns to a resting condition.

The following account refers to the heart muscle in order to better explain the action potential mechanism.

Myocardial activation normally begins with the spontaneous sodium calcium dependent depolarization of cells within the sinoatrial (SA) node located approximately at the junction of the right atrium and superior vena cava. The impulse then propagates in a wave-like fashion through the myocardium to the atrioventricular (AV) node located in the lower portion of the interatrial septum. Conducting through the AV node primarily involves the calcium-dependent process of depolarization and is delayed owing to membrane properties of the nodal cells.

The impulse is rapidly transmitted through the bundle of His, which then bifurcates into fibers The distal portion of the specialized conducting system is a network of smaller fibers, which delivers the propagated impulse to the non-specialized ventricular tissue, resulting in a synchronized myocardial contraction. The action potential of the bundle of His-Purkinje system and ventricular myocardium has five typical phases. In its resting state, the interior of most cardiac cells, with the exception of the sinus and AV nodes is approximately 80 to 90 mV negative with respect to a reference extracellular electrode. The resting membrane potential is primarily determined by the concentration gradient of potassium across the cell membrane. The concentration of intracellular potassium is approximately 30 times greater than its extracellular concentration, and it is the diffusion of this ion out of the cell that results in the resting transmembrane potential of approximately −90 mV in the fully repolarized state. The extracellular sodium concentration is approximately 15 times greater than its extracellular concentration, and the rapid influx of this ion into the cells results in the usual process of rapid cellular depolarization. The sodium channels rapidly inactivate and do not reactivate until the membrane potential is repolarized to less then −50 mV. A slower depolarization process may occur that predominantly involves calcium ions. The ionic species responsible for the action potential vary among the cardiac tissues, and the configuration of the action potential is therefore unique to each tissue.

The resting phase lasts until the cell is activated (phase 0). When an activation signal reaches the cell, the cell membrane is locally depolarized. If the depolarization reaches a certain threshold value, the cell membrane will rapidly depolarize within a few msec to a value of approximately 20 mV. The cell then rapidly partially repolarizes and the signal is reduced in about 10 mV, followed by further slow repolarization reducing the signal further by about 20 mV over a period of about 300 msec. The slower part of depolarization is called the plateau phase. The repolarization phases of the transmembrane action potential comprise phases 1–3. During the plateau period, the contraction of the muscle occurs. Finally, the cell reaches the resting membrane potential (phase 4).

Refractoriness is a property of the cells that defines the period of recovery that cells require before they can respond again to an excitation by a stimulus after being discharged. The absolute refractory period (ARP) is defined by the part of the action potential during which no stimulus, regardless of its strength, can evoke another response. The effective refractory period (ERP) is that part of the action potential where a stimulus can only evoke a local non-propagated response. The relative refractive period (RRP) extends from the end of the ERP to the instant in time when the tissue is fully recovered. During the RRP, a stimulus greater than the threshold strength is required to evoke a response which is propagated slowly in respect to the normal propagation. After the completion of the action potential cycle, excitability recovers and evokes responses that have characteristics similar to the spontaneous normal response.

Characteristics of the action potential in the heart muscle cells such as action potential duration, its amplitude or information regarding the refractory periods is of significant relevance. Online measurements of the action potential duration may allow monitoring the progress of a severe illness of the heart caused by cardiomyopathy. Moreover, it may be efficient in detecting and predicting the occurrence of arrhytmic events. Action potential duration measurements serve in the determination of the tissue viability, detection of eschemic changes, determination of drug effects, and monitoring effects of induced signals, such as pacing, deffibrilation, electrical tissue control. Attention is drawn to PCT Patent Application No. PCT/IL97/00012, published as WO 97/25098, which disclosed a method and apparatus for locally controlling the electrical and/or mechanical activity of cardiac muscle cells, in situ. Preferably a continuous control is applied, but alternatively, discrete application is possible too. Chronical action potential measurements in situ have the advantage of providing crucial information for the determination of the working parameters of the electrical muscle control administered in accordance with the above mentioned patent application, and in particular serve as a feedback channel to determine the efficiency of the administered control. The data obtained through action potential duration measurements can be also processed by the microprocessor of the apparatus described in the above mentioned patent application, and be used to determine the parameters of the induced electrical signal issued to the muscle by the apparatus its timing and sequence. It may also be used for safety considerations, to initiate the halting of any further electrical signal induction, upon identifying substantial changes in the localized refractory period.

The measurement of the global Q-T interval, from body ECG, provides an unreliable estimate of action potential duration, from the onset of ventricular depolarization to the end of the T wave. Refractory periods, which are reflected in the duration of cardiac action potential, vary from one myocardial region to another, The Q-T interval, which approximates the duration of electrical systole, is known to vary from one cardiac area to another. In patients with prolonged Q-T intervals, the variation from one site to another is much higher than the variation in normal subjects (see, for example, "Spatial Distribution of QT intervals: An alternative approach to QT dispersion", P. Van Leeuwen et al., PACE, Vol. 19, 1996, P. 1894–94, "Relation of human cardiac action potential duration to the interval between beats: implications for the validity of rate corrected QT interval (QTc)", W. A. Seed et al., Br Heart Journals 1987, 57, 32–7, and "Monophasic action potential mapping in human subjects with normal electrocardiograms: direct evidence for the genesis of the T wave", M. R. Franz et al., Circulation, Vol. 75, No. 2, 1987, 379–386).

Conventional bipolar and unipolar leads cannot be used to study the spatial and temporal sequences of localized repolarization. Prior art bipolar leads used in ECG fail to record sharp spikes typical of rapidly propagating excitation front. The typical drawbacks are summed up as follows; the measured signal is obtained over a very large area between two relatively distant locations (practically over the entire heart), polarization following the pulse prevents real measurement, the actual surface area of the conventional electrodes is too large, and consequently the resolution of the reading is relatively low.

A method for measuring in-vivo action potential, called monophasic action potential (MAP), was developed (see, for example U.S. Pat. No. 4,682,603 (Franz), filed Mar. 6, 1984, U.S. Pat. No, 4,955,382 (Franz et al.), filed Apr. 3, 1989, and U.S. Pat. No. 4,979,510 (Franz et al.), filed Jul. 27, 1988). MAP directly records the waveform of the beating heart from two separate electrodes MAP recordings had been obtained in humans from atrial and ventricular endocardial and epicardial sites. The disadvantage of this method is the short circuiting effect of damaged cells, which prevents the signal from advancing, and the relatively large number of cells in contact with the suction electrode, reduces the accuracy as it refers to a summation of the signal propagating over a large number of cells. Moreover, the use of plunge electrodes, suction electrodes and pressure contact electrodes, may induce the formation of scar tissue or connective tissue in the area connecting the electrode tip to the tissue. Furthermore it be chronically used, as after a short period of time the tissue becomes numb and looses its viability Therefore, this device is not suitable for intramural sites or for continuous or chronic recordings (over a long period of time). It should be also noted that MAP is an active measurement, which involves interefering actively with the natural activity of the cardiac tissue, and this can inflict bias on the results.

Some of the theories and experimental evidence on the use of monophasic action potential methods are disclosed in detail in Patent Application titled "Apparatus and Methods for Chronic Measurement of Monophasic Action Potential", Pat. No. 6,152,882.

BRIEF DESCRIPTION OF THE INVENTION

It is an object of the present invention to provide a sensor for the measurement of the action potential duration possessing the ability to estimate action potential duration and consequently the refractory periods in chronic situation in-vivo with high degree of accuracy.

It is another object of the present invention to provide a sensor for the measurement of the action potential duration which allows local measurement over a small number of tissue cells.

Yet another object of the present invention is to provide such a sensor for measurement of the action potential duration which allows continuous recordings.

It is another object of the present invention to provide such a sensor for the measurement of action potential duration which does not interfere with the natural activity of the cardiac tissue, and is employed passively.

An aspect of the present invention is the deployment of a bipolar electrode over a localized region of a muscle tissue, covering a small number of tissue cells.

It is therefore provided, in accordance with a preferred embodiment of the present invention, a bipolar sensor for a muscle action potential measurement comprising two electrodes, exposed at the distal end of an electrode lead, wherein said electrodes at said distal end are kept at a very close proximity, wherein the cross-section of said electrodes detection surface is very small, and wherein said sensor is electrically connected to an electrical reading device circuitry.

Furthermore, in accordance with another preferred embodiment of the present invention, the distance between said electrodes at the distal end of said lead is not more than 7 mm, and preferably not more than 2 mm.

Furthermore, in accordance with another preferred embodiment of the present invention, each of the two electrodes has detection surface area in the range of 0.1 and 3.0 mm sqr.

Furthermore, in accordance with another preferred embodiment of the present invention, the electrodes have substantially the same detecting surface area.

Furthermore, in accordance with another preferred embodiment of the present invention, the electrodes are separated by an electrically insulating material.

Furthermore, in accordance with another preferred embodiment of the present invention, the processing means is a part of an electrical tissue control system, and the data retrieved by the sensor is used to identify the length of the refractory period, and wherein the processing means determines, by applying a predetermined algorithm, the possible need for a change in the signals induced by said electrical tissue control system.

There is further provided, in accordance with another preferred embodiment of the present invention, a sensor for the measurement of action potential duration of muscle tissue, said sensor comprising two electrodes exposed at the distal end of an electrode lead, said electrodes surrounded by a guard-ring electrode, for screening noise or background signals, wherein said electrodes at said distal end are kept at a very close proximity, and wherein said sensor is electrically connected to a processing means for processing the signal detected by the sensor.

There is further provided, in accordance with another preferred embodiment of the present invention, a sensor for the measurement of action potential duration of muscle tissue, said sensor comprising two electrodes coaxially positioned at the distal end of an electrode lead, wherein said electrodes at said distal end are kept at a very close proximity, and wherein said sensor is electrically connected to a processing means for processing the signal detected by the sensor.

There is further provided, in accordance with another preferred embodiment of the present invention, a sensor for the measurement of action potential duration of muscle tissue, said sensor comprising two electrodes positioned at a side wall of an electrode lead, wherein said electrodes are kept at a very close proximity, and wherein said sensor is electrically connected to a processing means for processing the signal detected by the sensor.

There is further provided, in accordance with another preferred embodiment of the present invention, a sensor for the measurement of action potential duration of muscle tissue, said sensor comprising two electrodes positioned at a side wall of an electrode lead, confined by a pair of guard-ring electrodes, positioned at either sides of the two sensing electrodes, along the lead, and serve as guard rings, wherein said two electrodes are kept at a very close proximity, and wherein said sensor is electrically connected to a processing means for processing the signal detected by the sensor.

Furthermore, in accordance with another preferred embodiment of the present invention, the guard-ring electrodes are kept at equal potential.

And finally, in accordance with another preferred embodiment of the present invention, the processing means comprise two parallely electrically connected amplifiers, a low-band pass amplifier, said low-band pass amplifier having a frequency response optimally tuned to pass the repolarizarion signal, and a high-band pass amplifier, said high-band pass amplifier having a frequency response optimally tuned to pass the depolarization signal, wherein said amplifiers are parallely electrically connected to an analog-to-digital filter, and wherein said analog-to-digital filter's output is electrically connected to a micoporcessor unit.

BRIEF DESCRIPTION OF THE FIGURES

FIG. 3b depicts yet another configuration of an action potential duration measuring sensor, in a coaxial configuration, in accordance with a preferred embodiment of the present invention, incorporated with a pacing lead, provided with a guard ring.

DETAILED DESCRIPTION OF THE INVENTION AND FIGURES

The present invention relates to the estimation of action potential, and in particular action potential duration, of muscle tissues. More particularly it relates to a novel sensor designed for the chronic estimation of the local action potential duration, using close bipolar technique as described hereafter, in particular where it is used to measure cardiac action potential duration.

The present invention provides a novel design of a sensor for the measuring and estimating of action potential, and in particular action potential duration, by employing local activity measurements conducted on a small portion of the heart muscle. An aspect of the present invention is the deployment of a bipolar electrode over a localized region of a muscle tissue, covering a small number of tissue cells. The sensor is positioned in its target location by electrode leads, preferably navigated through the vasculature, and positioned epicardially or endocardially, depending on the clinical requirements.

A preferred embodiment of the sensor of the present invention is based on an electrode lead comprising the detecting electrodes, exposed at its distal end, to allow endocardial deployment. Optionally, in yet another preferred embodiment of the present invention, the detecting electrodes are exposed at the sidewall of the lead, close to its distal end, which enables epicardial use. Optionally, in another preferred embodiment of the present invention, the detecting electrode is attached to the muscle epicardially without passing through a vein, in a manner similar to the deployment of known epicardial electrodes in surgery. Furthermore, the sensor of the present invention may be incorporated in such surgically inserted electrodes. The use of the preferred embodiment having exposed electrodes at the distal end or the use of the preferred embodiment having exposed electrodes at the side-wall will depend on the preferred location of the implantation site, the heart muscle wall or the coronary veins, respectively. The electrodes are arranged in a configuration that enables receiving signals from a relatively small area of a muscle without loosing significant information. Hence, the chosen bipolar electrodes are small in dimensions, are placed close to the tissue and measure a differential signal between two cellular areas close together. The measurements provide high degree of correlation with the actual action potential duration that gives a close indication to the refractory period.

The action potential duration measuring sensor of the present invention is intended to measure the local muscle electrical activity in-vivo, obtaining a very high-resolution reading, as a result of its novel design. In order to obtain high resolution and more accurate readings, the sensing electrodes have to be very small in their cross-section area, and they should be positioned as close to each other as possible.

The sensor is electrically connected to a processing means for the processing of the signal picked up by the sensor. The processing means may optionally be a part of an electrical tissue control system, such as the electrical control systems described in PCT Patent Application No. PCT/IL97/00012, published as WO 97/26098.

Sensing and detecting signals from the bipolar electrodes can be done using ultra low noise differential sense amplifiers that can receive low signals, filter it and detect both the depolarization and repolarization activities wave fronts. Since the frequency response of the depolarization activity is different from the repolarization, it is preferred to use two parallel sense amplifiers, each with frequency response that fits the special characteristics of the corresponding signals, and combine the Information for the detection of depolarization and repolarization difference.

The electrodes are made of a conductive material, optionally carbon or platinum iridium or iridium oxide, and are electrically insulated to prevent any contact between them which would result in a short circuit.

The whole electrode lead is optionally provided with a jacket made of a biocompatible material, suitable for implantation or surgical use.

Figures 1A, 1B:
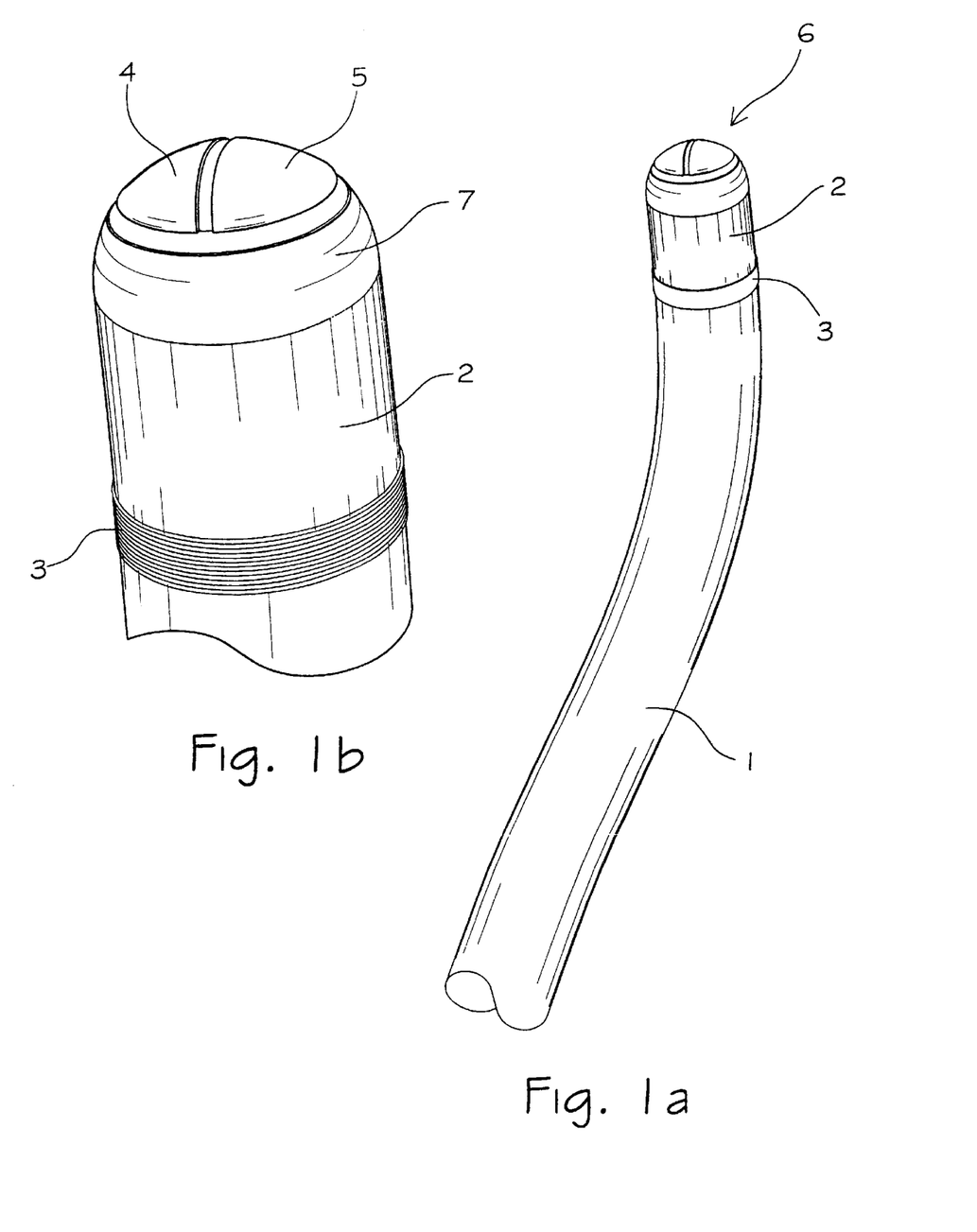
FIG. 1a, provides a general view of an action potential duration measuring sensor, in a side-by-side configuration, in accordance with a preferred embodiment of the present Invention, incorporated with a pacing lead.
FIG. 1b depicts the distal tip of said pacing lead showing in details the sensing electrodes, in a side-by-side configuration.

Reference is now made to FIG. 1a, providing a general view of an action potential duration measuring sensor, in accordance with a preferred embodiment of the present invention, incorporated with a pacing lead.

The electrode lead (1), suitable for intravascular catheterization, has at its distal end (2) a pacing electrode cap (6), and a ring electrode (3). FIG. 1b depicts the distal tip of the lead (2) showing the sensing electrodes in detail. The cap (6) is divided electrically into 3 electrodes: at the distal end two sensing electrodes (4, 5), placed side by side, and at the periphery a third electrode (7), used for pacing signals. The three electrodes are all separated and electrically insulated. The peripheral electrode (7) and ring electrode (3) may be a part of the pacing system, or electrodes used to deliver contractility control signals. The sensing electrodes (4, 5) are connected to the measuring device circuitry (not showing in FIG. 1) by means of electrical wiring passing through the lead (1) all the way to its proximal end which can be connected to a processing unit. The sensing electrodes (4, 5), may be incorporated in a pacing electrode, or contractility control electrode, thus allowing the delivery of signals to the muscle tissue using these electrodes.

As shown in FIG. 1b, the electrodes (4, 5) should preferably have the same detecting surface area. The detection surface area of each of the sensing electrodes is preferably in the range of between 0.1 and 3 mm sqr. Matching of the two sensing electrodes surface area can be achieved by chemical etching or laser trimming of the electrode surface. The distance between the electrodes should be as small as possible, in order to be able to pick up a signal from as little cells as possible. It should be noted that ideally it is desired to read the signal over a single cell, but as a typical human cardiac muscle cell is in the order of 200 microns, it may be impractical. If the sensor of the present invention is to be chronically implanted in the patient's body, then the width of the sensor (and in effect, the distance between the sensing electrodes) is limited by the width of the blood vessel through which it is guided to the desired position, at its narrowest portion. If the sensor of the present invention is to be employed during a surgery, then the width of the blood vessels may no longer pose a limitation, but it is understood that a distance between the sensing electrodes of more than 7 mm would be undesired, as it would cover to many cells (some 30–40 human muscle cells are covered by 7 mm), and therefore not comprise a local reading, as desired. Preferably the distance between the sensing electrodes should not exceed 2 mm. Such a distance within the electrodes would contain a small number of cells—in the order of 10 cells.

Figures 2A, 2B:
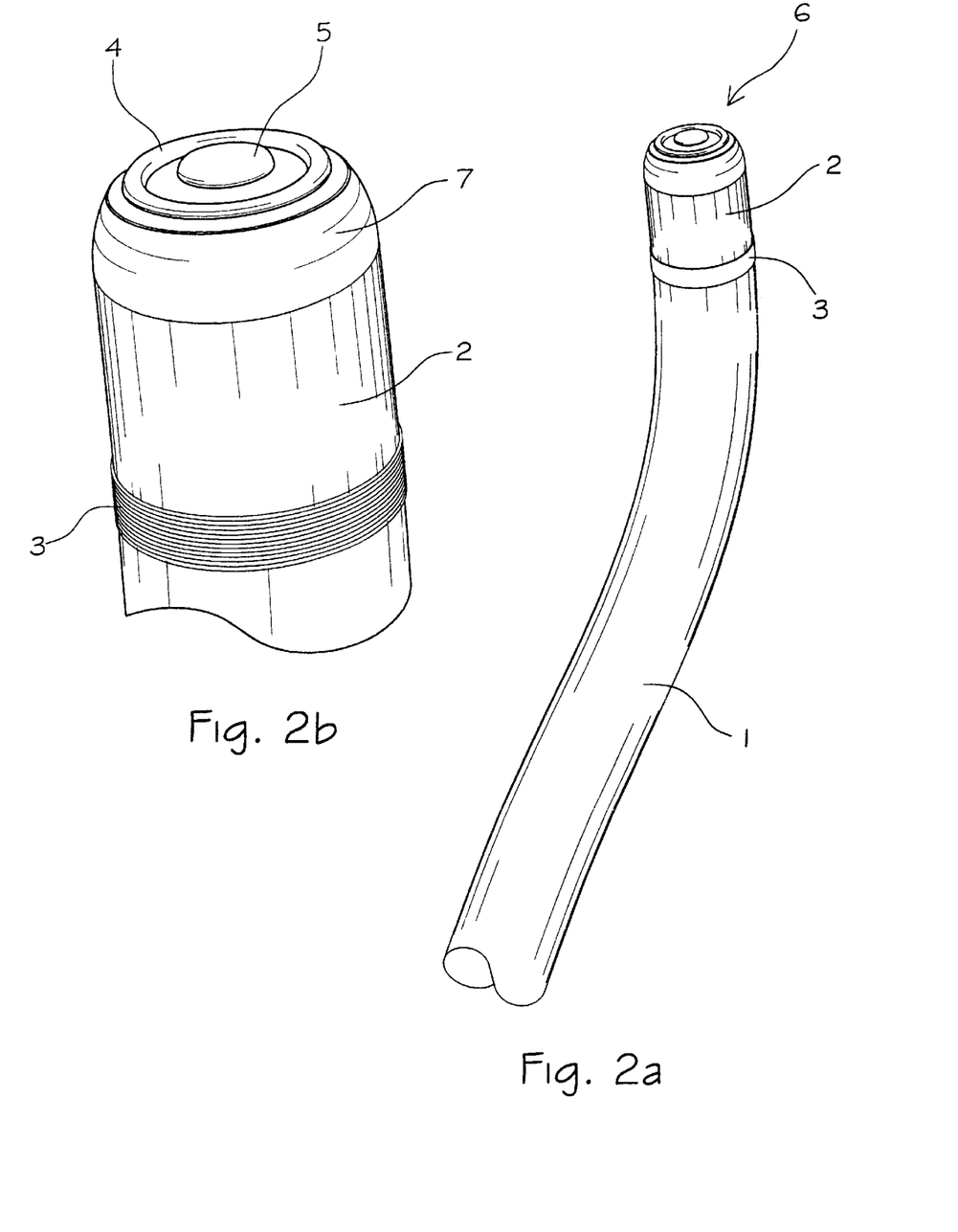
FIG. 2a, provides a general view of an action potential duration measuring sensor, in a coaxial configuration, in accordance with a preferred embodiment of the present invention, incorporated with a pacing lead.
FIG. 2b depicts the distal tip of said pacing lead showing in details the sensing electrodes, in a coaxial configuration.

Reference is now made to FIG. 2a, providing a general view of an action potential duration measuring sensor, in a coaxial configuration, in accordance with a preferred embodiment of the present invention, incorporated with a pacing lead.

The electrode lead (1) has at its distal end (2) a pacing electrode cap (6), and a ring electrode (3). FIG. 2b depicts the distal tip of the lead (2) showing the sensing electrodes in detail.

The electrode cap (6) is divided electrically into 3 electrodes: at the distal end two sensing electrodes (4, 5), placed in a coaxial configuration, and at the periphery a third electrode (7), used for pacing signals. The three electrodes are all separated and electrically insulated. The peripheral electrode (7) and ring electrode (3) can be used as a part of the pacing system or a contractility control signal delivery system. The sensing electrodes (4, 5) are connected to the measuring device circuitry (not showing in FIG. 1) by means of electrical wiring passing through the lead (1) all the way to its proximal end which is connected to a processing means. The processing means may optionally be incorporated as a part of an electrical tissue control system, such as the electrical control systems described in PCT patent application No. PCT/IL97/00012, published as WO 97/25098. The data retrieved by the sensor can be used by such an electrical tissue control system to identify the length of the refractory period, and the processing means can then determines, by applying a predetermined algorithm, the possible need for a change in the signals induced by the electrical tissue control system.

The sensing electrodes should preferably have the same detecting surface area. The detection surface area of each of the sensing electrodes is preferably in the range of between 0.1 and 3 mm sqr. The distance between the electrodes should be as small as possible, In order to be able to pick up a signal from as little cells as possible. As mentioned before, it should be noted that ideally it is desired to read the signal over a single cell, but as a typical human cardiac muscle cell is in the order of 200 microns, it may be impractical. If the sensor of the present invention is to be chronically implanted in the patient's body, then the width of the sensor (and in effect, the distance between the sensing electrodes) is limited by the width of the blood vessel through which it is guided to the desired position, at its narrowest portion. If the sensor of the present invention is to be employed during a surgery, then the width of the blood vessels may no longer pose a limitation, but it is understood that a distace between the sensing electrodes of more than 7 mm would be undesired, as it would cover to many cells (some 30–40 human muscle cells are covered by 7 mm), and therefore not comprise a local reading, as desired. Preferably the distance between the sensing electrodes should not exceed 2 mm. Such a distance within the electrodes would contain a small number of cells—in the order of 10 cells.

The benefit in this latter annular configuration is in that it eliminates the sensor's direction preference, as the detected signal can travel in any direction. This enhances the reliability of the measurement.

Figure 3A:
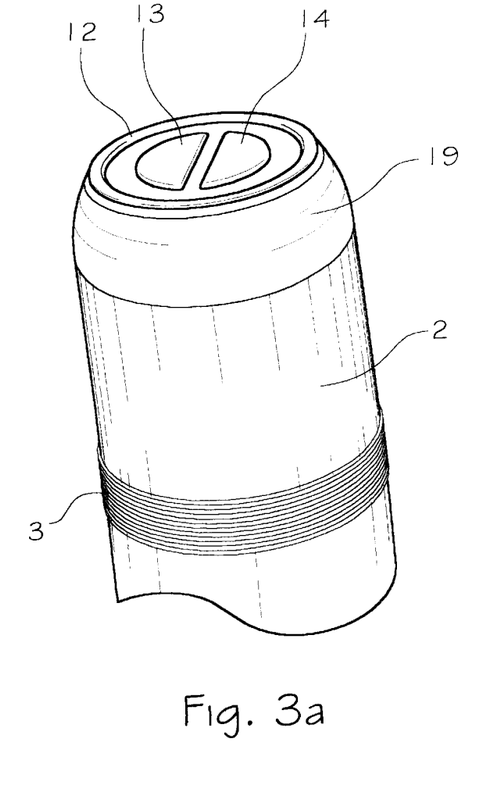
FIG. 3a depicts yet another configuration of an action potential duration measuring sensor, in a side-by-side configuration, in accordance with a preferred embodiment of the present invention, incorporated with a pacing lead, provided with a guard ring.

FIG. 3a depicts yet another configuration of an action potential duration measuring sensor, in a side-by-side configuration, in accordance with a preferred embodiment of the present invention, incorporated with a pacing lead, provided with a guard ring.

The sensing electrodes (13, 14), placed side-by-side, are surrounded 20 by a guard ring (12), which is in fact another electrode, used for screening noise or background signals, for example far field signal resulting from propagation of action potential in a different region of the muscle. The guard ring is itself optionally enclaved within an electrode (19) such as a pacing electrode. The guard ring is used to prevent background signals or noise from affecting the reading of the sensor. The sensing electrodes may optionally be also used as signal delivery electrodes.

FIG. 3b depicts yet another configuration of an action potential duration measuring sensor, in a coaxial configuration, in accordance with a preferred embodiment of the present invention, incorporated with a pacing lead, provided with a guard ring. The sensing electrodes (16, 17)

are arranged in a coaxial configuration, and surrounded by a guard ring (15), to prevent any noise or background signals from interfering in the sensor readings. Optionally, this arrangement is placed within an electrode (18), such as a pacing electrode or any other type of electrode.

Again, the electrodes should preferably have the same detecting surface area. The detection surface area of each of the sensing electrodes is preferably in the range of between 0.1 and 3 mm sqr. The distance between the electrodes should be as small as possible, in order to be able to pick up a signal from as little cells as possible. The distace between the sensing electrodes should be not more than 7 mm, and preferably it should not exceed 2 mm.

Figure 4A:
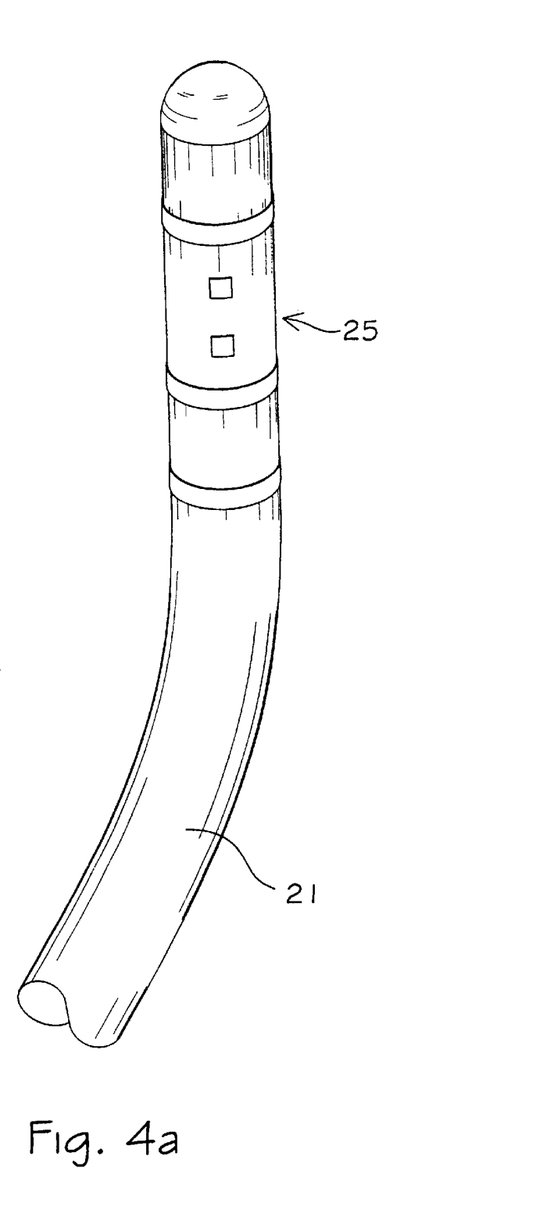
FIG. 4a illustrates yet another preferred embodiment of an action potential duration measuring sensor, in accordance with the present invention, here positioned on the side-wall of a pacing lead.
Figure 4B:
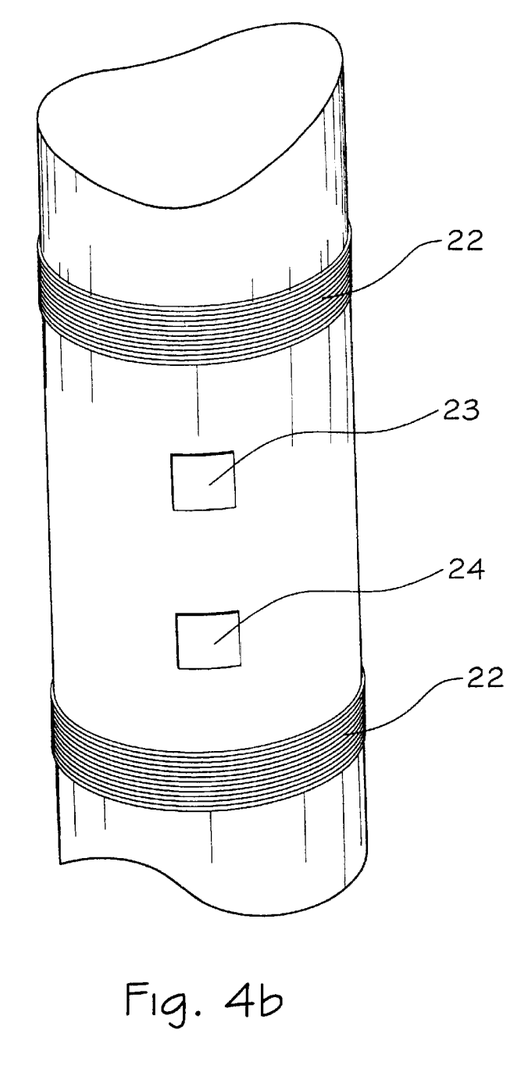
FIG. 4b depicts the sensing electrode configuration of the action potential duration measuring sensor positioned on the side-wall of a pacing lead (of FIG. 4a).

FIG. 4a illustrates yet another preferred embodiment of an action potential duration measuring sensor, in accordance with the present invention, here positioned on the side-wall of an electrical tissue controller signal delivery electrode or a pacing lead. FIG. 4b depicts the sensing electrode configuration of the action potential duration measuring sensor positioned on the side-wall of a pacing lead (of FIG. 4a). An electrode lead (21 in FIG. 4a) has a sensing region (25), which is shown magnified in FIG. 4b. Two sensing electrodes (23, 24) are placed side by side along the side wall of the electrode lead. The sensing electrodes (23, 24) confined by a pair of ring electrodes (22), positioned at either sides of the two sensing electrodes, along the lead, and serve as guard rings. The ring electrodes (22) are made to be of equal potential (preferably earthed) in order to prevent background signals or noise from interfering with the readings of the sensor. The sensing electrodes themselves can optionally comprise two ring electrodes, instead of those shown in FIG. 4. The distance between the sensing electrodes in this side-wall configuration is not limited to the width of the blood vessel through which the sensor is guided to its position, but from the same considerations as mentioned with reference to the embodiment shown in FIG. 1, it should not exceed 7 mm, and preferably be not more than 2 mm.

The lead itself is optionally provided with an electrically insulating jacket (16) made of a biocompatible material to ensure a safe in-vivo operation of the lead inside the patient's body.

The electrode lead carrying the action potential duration measuring sensor of the present invention may be actively or passively fixed to the muscle tissue, to enable an effective contact of the sensing electrodes and the tissue.

The signals expected to be collected using the action potential duration measuring sensor of the present invention are usually in the range of 0.1 to 6 mV. Induced signals (such as pacing signals) expected to be collected by the action potential duration measuring sensor range typically from 1 to 30 mV.

The lead carrying the action potential duration measuring sensor of the present invention should be attached to the surface of the heart muscle tissue in order to enable a sufficient physical contact between the electrodes and the tissue. There are several types of active-fixation and passive-fixation designs suitable for the fixation of the electrode lead carrying the action potential duration measuring sensor of the present invention, and these are chosen in accordance with the actual clinical configurational requirements (i.e. depending on whether endocardial or epicardial implantation is considered).

Figure 5:
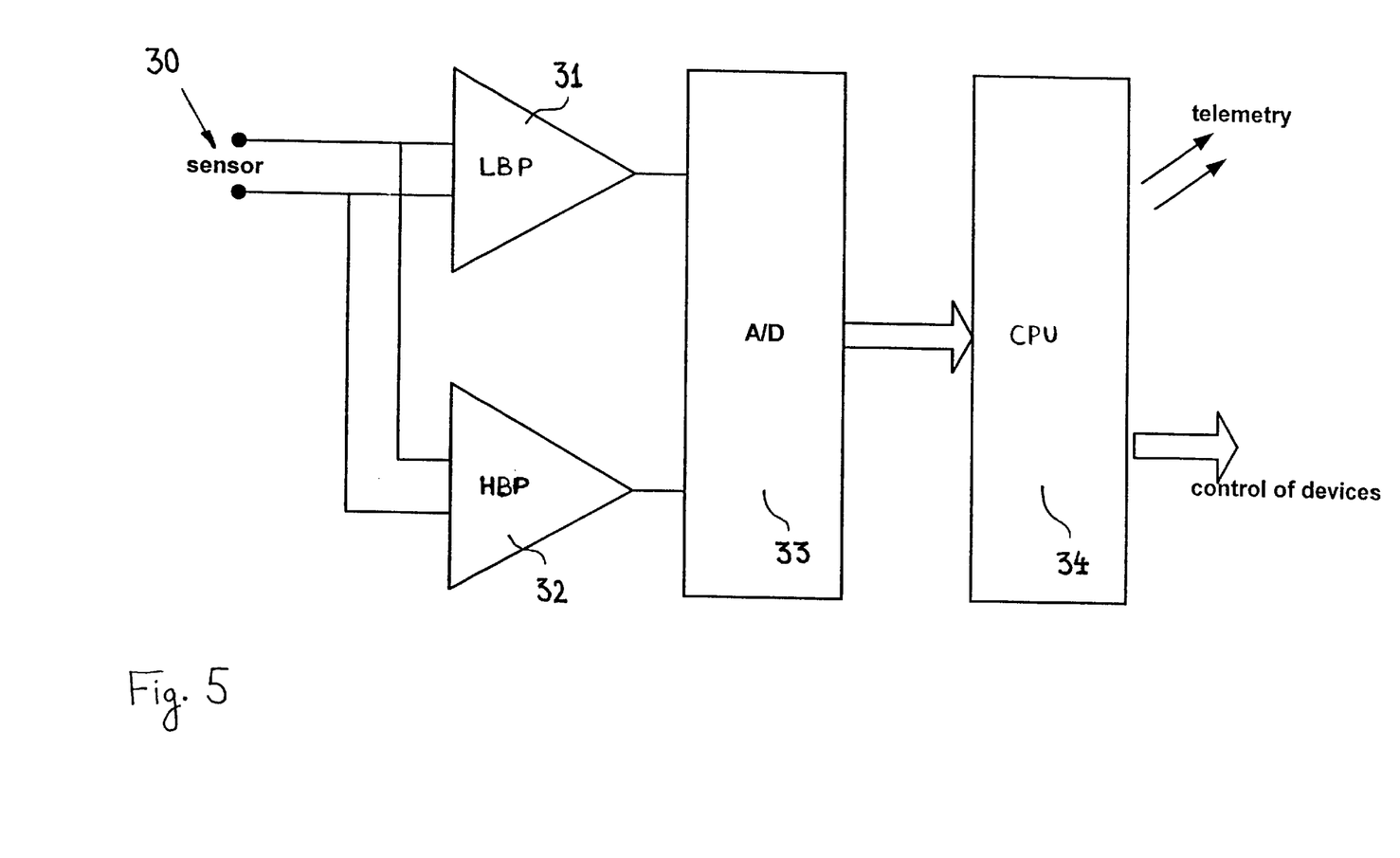
FIG. 5 illustrates a schematic diagram of an optional configuration of an electrical circuitry to which a sensor for the measurement of action potential duration, in accordance with a preferred embodiment of the present invention, is electrically connected.

Reference is made to FIG. 5 illustrates a schematic diagram of an optional configuration of an electrical circuitry to which a sensor for the measurement of action potential duration, in accordance with a preferred embodiment of the present invention, is electrically connected. A sensor (30) for the measurement of action potential duration, in accordance with a preferred embodiment of the present invention, is electrically parallely connected to a low-band pass (LBP) amplifier (31), with a frequency response tuned to allow optimal pickup of the local repolarization signal, and a high-band pass (HBP) amplifier (32), with a frequency response tuned to allow optimal pickup of the local depolarization signal. When a signal is picked up by the sensor (30) it is transmitted to the amplifiers. If the signal is in the low band range (depolarization) it is amplified by the LBP amplifier (31), and if the signal is in the high band range (repolarization) it is amplified by the HBP amplifier (32). The amplified signal is then transmitted to an analog-to-digital (A/D) filter (33), which is predesigned to allow the passage of the signal of a threshold amplitude (omitting noise or far location background signals), to a microprocessor unit (34). The microprocessor unit processes the data, detect the local activities and estimate local potential duration from the sampled data. The processor may output, in accordance with a predetermined programmed algorithm, control commands to other devices, such as pacing, deffibrilation, or electrical tissue control devices. Optionally the processed data may be transmitted to remote devices by telemetry.

It should be clear that the description of the embodiments and attached Figures set forth in this specification serves only for a better understanding of the invention, without limiting its scope as covered by the following claims.

It should also be clear that a person skilled in the art, after reading the present specification could make adjustments or amendments to the attached Figures and above described embodiments that would still be covered by the following Claims.

What is claimed is:

1. A sensor processing system for the measurement of action potential duration of muscle tissue, said system comprising a sensor comprising two electrodes positioned at a side wall of an electrode lead, confined by a pair of guard-ring electrodes provided with earthing means for earthing the guard-ring electrodes, said pair of guard rings being positioned at either side of the two sensing electrodes along the lead, and serving as guard rings, wherein said two electrodes are kept at a very close proximity, and wherein the sensor is electrically connected to a processing means for processing the signal detected by the sensor.

2. The sensor processing system according to claim 1, wherein the processing means comprise first and second parallelly electrically connected amplifiers, the first amplifier being a low-band pass amplifier having a frequency response corresponding to typical repolarization frequencies and the second amplifier being a high-band pass amplifier having a frequency response corresponding to typical depolarization frequencies, wherein said amplifiers are parallelly electrically connected to an analog-to-digital filter, and wherein said analog-to-digital filter outputs a signal to a microprocessor unit.

3. A sensor for the measurement of action potential duration of muscle tissue electrically connectable to processing means, said sensor comprising two electrodes positioned at a side wall of an electrode lead, confined by a pair of guard-ring electrodes provided with earthing means for earthing the guard-ring electrodes, the guard ring electrodes being positioned at either side of the two sensing electrodes along the lead, and serving as guard rings, wherein said two electrodes are kept at a very close proximity.

* * * * *